US00PP19361P2

(12) United States Plant Patent
Takeshita

(10) Patent No.: US PP19,361 P2
(45) Date of Patent: Oct. 21, 2008

(54) ***NEMESIA* PLANT NAMED 'KIRINE-34'**

(50) Latin Name: *Nemesia hybrida*
Varietal Denomination: Kirine-34

(75) Inventor: Daigaku Takeshita, Tochigi-ken (JP)

(73) Assignee: Kirin Agriobio Co. Ltd, Tokyo (JP)

( * ) Notice: Subject to any disclaimer, the term of this patent is extended or adjusted under 35 U.S.C. 154(b) by 0 days.

(21) Appl. No.: 11/895,939

(22) Filed: Aug. 28, 2007

(51) Int. Cl.
*A01H 5/00* (2006.01)

(52) U.S. Cl. ..... Plt./458

(58) Field of Classification Search ..... Plt./458
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Nemesia* plant named 'Kirine-34', characterized by its upright, outwardly spreading and uniformly mounded growth habit; freely branching and flowering plant habit; large bright yellow-colored flowers; relatively tolerant to high temperatures; and good garden performance.

2 Drawing Sheets

Botanical designation: *Nemesia hybrida.*
Cultivar denomination: 'KIRINE-34'.

BACKGROUND OF THE INVENTION

The present invention relates to a new and distinct cultivar of Nemesia, botanically known as *Nemesia hybrida* and hereinafter referred to by the name 'Kirine-34'.

The new *Nemesia* is a product of a planned breeding program conducted by the Inventor in Tochigi, Japan, The objective of the breeding program is to create new *Nemesia* cultivars with good vigor and attractive flower coloration.

The new *Nemesia* originated from a cross-pollination made by the Inventor in February, 2005 in Tochigi, Japan of the *Nemesia hybrida* cultivar Aromatica Compact White, not patented, as the female, or seed, parent with the *Nemesia strumosa* cultivar Sundrop Yellow, not patented, as the male, or pollen, parent. The new *Nemesia* was discovered and selected by the Inventor as a single flowering plant within the progeny of the stated cross-pollination in a controlled environment in Tochigi, Japan in October, 2005.

Asexual reproduction of the new *Nemesia* by terminal cuttings in a controlled environment in Tochigi, Japan since November, 2005, has shown that the unique features of this new *Nemesia* are stable and reproduced true to type in successive generations.

SUMMARY OF THE INVENTION

The cultivar Kirine-34 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kirine-34'. These characteristics in combination distinguish 'Kirine-34' as a new and distinct cultivar of *Nemesia:*

1. Upright, outwardly spreading and uniformly mounded growth habit.
2. Freely branching and flowering plant habit.

3. Large bright yellow-colored flowers.
4. Relatively tolerant to high temperatures.
5. Good garden performance.

Plants of the new *Nemesia* differ from plants of the female parent, the cultivar Aromatica Compact White, in the following characteristics:

1. Plants of the new *Nemesia* are larger than plants of the cultivar Aromatica Compact White.
2. Plants of the new *Nemesia* have larger flowers than plants of the cultivar Aromatica Compact White.
3. Plants of the new *Nemesia* and the cultivar Aromatica Compact White differ in flower color as plants of the cultivar Aromatic Compact White have white-colored flowers.

Plants of the new *Nemesia* differ from plants of the male parent, the cultivar Sundrop Yellow, in the following characteristics:

1. Plants of the new *Nemesia* are larger than plants of the cultivar Sundrop Yellow.
2. Flowers of plants of the new *Nemesia* are fragrant whereas flowers of plants of the cultivar Sundrop Yellow are not fragrant.
3. Plants of the new *Nemesia* are more tolerant to high temperatures than plants of the cultivar Sundrop Yellow.

Plants of the new *Nemesia* can be compared to plants of the cultivar Kirine-1, disclosed to U.S. Plant Pat. No. 18,267. In side-by-side comparisons conducted by the Inventor in Tochigi, Japan, plants of the new *Nemesia* differed from plants of the cultivar Kirine-1 in the following characteristics:

1. Plants of the new *Nemesia* were more mounding than plants of the cultivar Kirine-1.
2. Plants of the new *Nemesia* had shorter internodes than plants of the cultivar Kirine-1.
3. Plants of the new *Nemesia* and the cultivar Kirine-1 differed in flower color as plants of the cultivar Kirine-1 had lighter yellow-colored flowers.
4. Plants of the new *Nemesia* were more high temperature tolerant than plants of the cultivar Kirine-1.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia.*

The photograph on the first sheet comprises a side perspective view of a typical flowering plant of 'Kirine-34' grown in a container.

The photograph on the second sheet is a close-up view of a typical flower of 'Kirine-34'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the spring in a polyethylene-covered greenhouse in Santa Paula, Calif. for about 13 weeks in containers. During the production of the plants, day temperatures averaged 26° C., night temperatures averaged 12° C. and light levels ranged from 4,000 to 5,000 foot-candles. Plants were pinched one time about two weeks after planting.

Botanical classification: *Nemesia caerulea* cultivar Kirine-34.

Parentage:

*Female, or seed, parent.*—*Nemesia caerulea* cultivar Aromatica Compact White, not patented.

*Male, or pollen, parent.*—*Nemesia strumosa* cultivar Sundrop Yellow, not patented.

Propagation:

*Type.*—By terminal cuttings.

*Time to initiate roots, summer.*—About three days at 27° C.

*Time to initiate roots, winter.*—About six days at 21° C.

*Time to produce a rooted young plant, summer.*—About three weeks at 27° C.

*Time to produce a rooted young plant, winter.*—About four weeks at 21° C.

*Root description.*—Fine, fibrous; white in color.

*Rooting habit.*—Freely branching; moderately dense.

Plant description:

*Plant and growth habit.*—Upright, outwardly spreading and uniformly mounded growth habit. Freely branching; about ten primary branches per plant and numerous secondary branches. Vigorous growth habit.

*Plant height.*—About 17 cm.

*Plant diameter.*—About 25 cm.

Lateral branch description:

*Length.*—About 16 cm.

*Diameter.*—About 2 mm.

*Internode length.*—About 3.5 cm.

*Strength.*—Strong.

*Aspect.*—Upright to outwardly spreading.

*Texture.*—Scattered pubescence.

*Color.*—147B.

Foliage description:

*Arrangement.*—Opposite, simple; sessile.

*Length.*—About 5 cm.

*Width.*—About 1.2 cm.

*Shape.*—Elliptical.

*Apex.*—Acute.

*Base.*—Acute.

*Margin.*—Slightly serrate.

*Texture, upper and lower surfaces.*—Smooth, glabrous.

*Venation pattern.*—Pinnate; arcuate.

*Color.*—Developing foliage, upper and lower surfaces: 146B. Fully expanded foliage, upper surface: 146A; venation, 146A. Fully expanded foliage, lower surface: 146B; venation, 146B.

Flower description:

*Flower arrangement and habit.*—Zygomorphic solitary flowers arranged on terminal racemes; flowering acropetally towards the apex. Flowers bilabiate. Flowers face upright and outwardly. Flowers last about five to seven days on the plant. Flowers not persistent. Freely flowering habit with about 12 to 14 flowers per raceme.

*Fragrance.*—Faint; floral.

*Natural flowering season.*—In California, plants flower from early spring to fall; flowering continuous during this period.

*Inflorescence height.*—About 6.5 cm.

*Inflorescence diameter.*—About 4 cm by 5.5 cm.

*Flower height.*—About 3 cm.

*Flower width.*—About 2.8 cm.

*Flower depth.*—About 1.8 cm.

*Flower buds.*—Shape: Ovoid. Length: About 1.4 cm. Diameter: About 5 mm to 7 mm. Color: 10D.

*Petals.*—Arrangement: Five petals; four upper petals are fused at base to form an upright lobed and arched banner lip; lower petal modified into a larger lip with convex oval protuberance with serves as a pollinator nectar guide and landing platform. Shape: Oval to rounded. Apex: Rounded. Margin: Entire; lower lip, slightly sinnuate. Length: Upper petals: About 1.2 cm to 1.4 cm. Lower petal: About 1.5 cm. Width: Upper petals: About 8 mm to 10 mm. Lower petal: About 2.2 cm. Texture, upper and lower surfaces: Smooth, glabrous. Color, upper and lower petals: When opening, upper surface: 17B. When opening, lower surface: 16D. Fully opened, upper surface: Upper petals, 23A; nectar guides at the base, 96D; lower petal, 23A; protuberance, 25A. Fully opened, lower surface: 16C.

*Sepals.*—Arrangement: Calyx star-shaped with five sepals fused at the base. Shape: Lanceolate. Apex: Acute. Margin: Entire. Length: About 6 mm. Width: About 2 mm. Texture, upper and lower surfaces: Pubescent. Color, upper and lower surfaces: 146A.

*Peduncles.*—Length: About 3.5 cm. Diameter: About 1.5 mm. Angle: Erect to about 45° from vertical. Strength: Strong. Texture: Scattered pubescence. Color: 146A.

*Pedicels.*—Length: About 2.4 cm. Diameter: Less than 1 mm. Angle: About 45° from peduncle axis. Strength: Moderately strong. Texture: Pubescent. Color: 146B.

*Reproductive organs.*—Stamens: Quantity/arrangement: Four per flower. Filament length: About 1.5 mm to 4 mm. Filament color: 155D. Anther shape: Oval. Anther length: Less than 1 mm.

Anther color: 17A. Pollen amount: Scarce. Pollen color: 162A. Pistils: Quantity: One per flower. Pistil length: About 2 mm. Style length: About 1 mm. Style color: 145C. Stigma shape: Rounded. Stigma color: 145B. Ovary color: 146B. Seed/fruit: Seed and fruit development have not been observed on plants of the new *Nemesia*.

Pathogen/pest resistance: Plants of the new *Nemesia* have not been observed to be resistant to pests and pathogens common to *Nemesia*.

Garden performance: Plants of the new *Nemesia* have been observed to tolerate wind and rain and have good garden performance.

Temperature tolerance: Plants of the new *Nemesia* have been observed to tolerate temperatures from about 0° C. to about 28° C.

It is claimed:

1. A new and distinct *Nemesia* plant named 'Kirine-34' as illustrated and described.

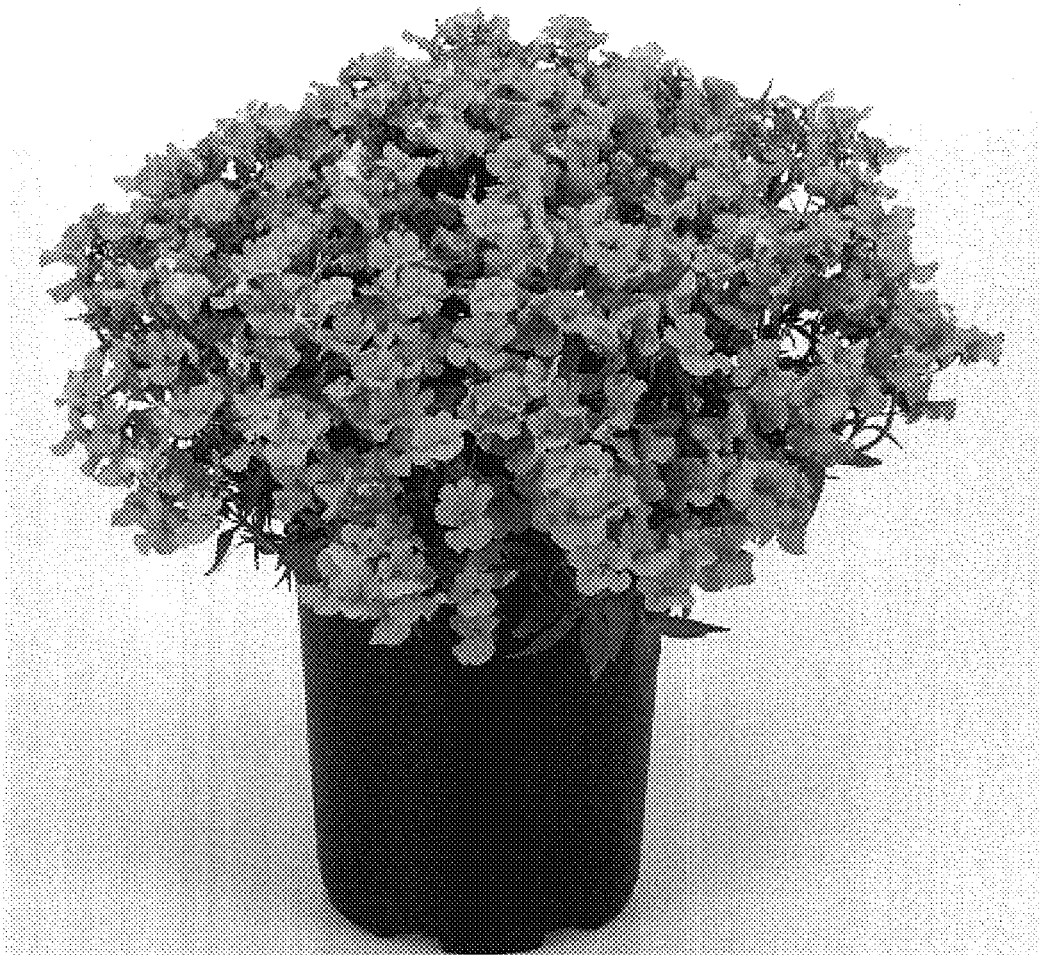

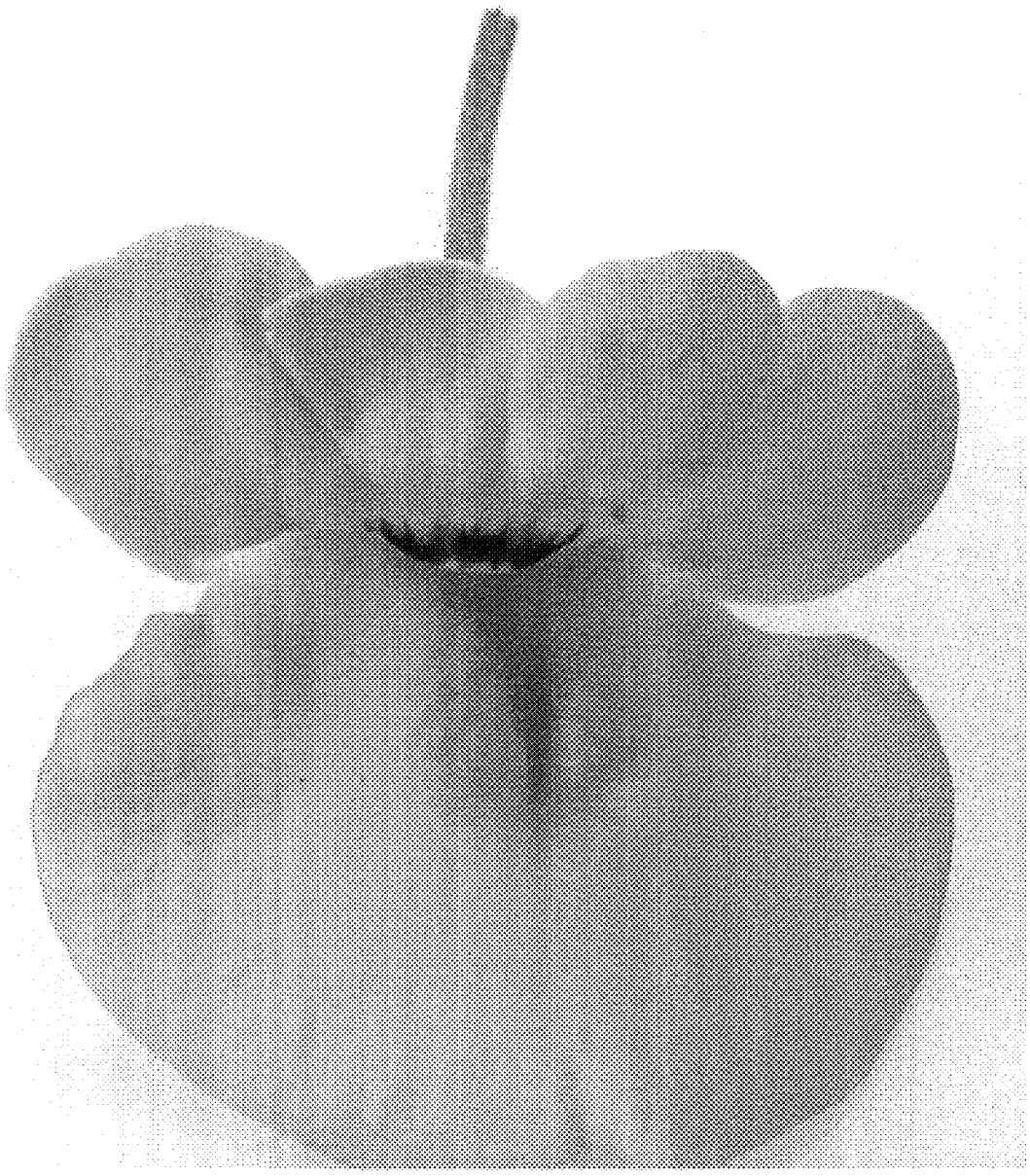

* * * * *